United States Patent [19]

Brooks

[11] Patent Number: Plant 6,362

[45] Date of Patent: Nov. 1, 1988

[54] PEAR TREE OLD HOME×FARMINGDALE VARIETY NO. 87

[75] Inventor: Lyle A. Brooks, Forest Grove, Oreg.

[73] Assignee: Gordon Bailey, Dayton, Oreg.

[21] Appl. No.: 923,028

[22] Filed: Oct. 24, 1986

[51] Int. Cl.[4] ..... A01H 5/03

[52] U.S. Cl. ..... Plt./36

[58] Field of Search ..... Plt./36

*Primary Examiner*—Robert E. Bagwill

*Attorney, Agent, or Firm*—Chernoff, Vilhauer, McClung & Stenzel

[57] ABSTRACT

This invention relates to a new and distinct variety of pear tree which is useful as a size-controlling rootstock. The new variety originated as a single seedling selected from a large group of pear seedlings which were grown from open-pollinated seed. This seed was collected from Old Home Pear Trees (*Pyrus communis*) growing in an isolated planting with Farmingdale pollinizers. Pear fruiting varieties propagated on the under stock of this new rootstock variety are approximately 80% of the size of like pear trees growing on domestic Bartlett seedling rootstocks. This "semi-dwarfing" selection is easily asexually reproduced; particularly by hardwood cuttings. It has proven to be graft compatible with all commercially grown pear varieties. It was selected for its non-rootsuckering habit, its resistance to Fireblight disease and its tolerance of Pear Decline disease. It has also proven to be hardy, early bearing and well anchored in the many areas and soil types where it was tested. It has proven to be adaptable to Northern pear growing areas such as Summerland, British Columbia, Harrow, Ontario, and Kentsville, Nova Scotia, Canada, having been selected to fill these Northern pear growing rootstock needs.

2 Drawing Sheets

BACKGROUND AND SUMMARY OF THE INVENTION

The original plant of this new variety was a member of a family of over 2000 pear seedlings which germinated from seeds obtained from the Canadian Department of Agriculture Research Unit located near Summerland, British Columbia, Canada. This seed, collected from open-pollinated Old Home pear trees (*Pyrus communis*) which were growing in an isolated experimental planting with Farmingdale pollinizers, was planted by the inventor in his nursery at Forest Grove, Oreg. in 1952.

Experimental objectives were to develop, by trial and selection, a series of clonal pear rootstocks which would fulfill several urgent needs of the orchardist and the nurserymen. The most important and immediate needs were for rootstocks that are resistant to Fireblight (*Erwina amylovora*) a common, debilitating bacterial disease of pear trees. Also needed were rootstocks that are tolerant of the more recently described and equally destructive disease of pear known as Pear Decline (Moria). Pear Decline is a mycoplasma-caused disease which plugs pear phloem sieve tubes below the graft union causing decline and death of trees. This is particularly true if pear trees are propagated on non-tolerant seedling rootstocks. Most rootstocks used for pear tree propagation today are considered susceptible to this virus-like disease.

Another objective of this work was to select from the seedling population, rootstock clones which would root readily in a nursery by cutting and/or by other negative means.

An additional objective was to select from this seedling population a series of growth-controlling rootstock clones which could be made available to nurserymen and growers and which would permit them to develop orchards using tree spacing techniques tailored to known uniform tree sizes. This objective can be accomplished only through the use of clonally propagated rootstocks.

All of these qualities are lacking in the seedling rootstocks currently being used by most nurserymen in the trade today. Old Home×Farmingdale No. 87 has shown its usefulness by exhibiting the following characteristics which fulfill all of the original desired objectives and in addition has shown itself to be particularly well adapted to the climatic and soil characteristics of Northern pear growing districts in Canada. It has been chosen to fill these needs following over 30 years of orchard and nursery testing and evaluation.

Final selection was made in 1985 following tests which consisted of trial plantings and nursery evaluations which were carried out at Summerland, British Columbia; Harrow, Ontario; Kentville, Nova Scotia; Yakima, Wash.; Geneva, N.Y.; and Hood River, Salem, Medford, Corvallis, Dayton and Forest Grove, Oreg.

TEST AND EVALUATION RESULTS

1. Pear varieties grown on the rootstock of this variety are approximately 80% of the size of like pear trees grown on the most commonly used commercial pear rootstock. These are seedling rootstocks of domestic Bartlett seed, also known as domestic pear seedlings (*Pyrus communis*). Trees grown on Bartlett seedling rootstocks are considered "standard" in size when established in the orchard and are used for the basis of all of our comparisons and measurements herein.

2. Due to its Old Home parentage, rootstocks of this variety have proven to be very Fireblight-resistant in all areas where tested. In one arbitrary range of resistance, with Bartlett seedlings rated zero, this clone was rated as 97% resistant to the disease.

3. Pear trees grown on the rootstock of this variety have shown no Pear Decline symptoms in all tests and in all areas where trial plantings were observed. Is believed to be Pear Decline-tolerant with all major commercial varieties. In comparison, Decline symptoms were noted on trees grafted on domestic Bartlett seedlings as well as on several other seedling rootstock types being evaluated.

4. The new variety of pear rootstock has been virus-indexed and found to be free of all known virus diseases of pear.

5. Only 2% of trees propagated on the new variety rootstock were observed to produce rootsuckers following close inspection over a 20-year period.

6. Yield efficiency, determined by comparing yield to unit of tree size was rated 9% above that of trees on domestic Bartlett seedling stocks.

7. Young Bartlett trees propagated on this new rootstock variety have come into bearing at an earlier age than similar trees grafted on domestic seedling stocks.

8. Many Bartlett test trees bloomed heavily and set fruit during their third growing season. This was compared to Bartlett trees on seedling stocks with light sporadic sets of fruit in their fourth growing season.

9. The new variety of rootstock is hardy in all areas where it was tested and is considered to be hardy wherever pears are grown.

10. The new rootstock variety is graft-compatible with all major commercially-grown pear varieties.

11. Pear varieties grown on the new rootstock variety show good root anchorage in the nursery and in the orchard.

12. The new rootstock variety shows only average resistance to pear root aphids.

13. The new variety is easily propagated by hardwood and softwood cuttings or by micropropagation methods (meristematic tissue culture). Such asexual reproductions have demonstrated that its distinctive characteristics and particularly including its "semi-dwarfing" character are stable and are transmitted without change through succeeding propagations and generations.

BRIEF DESCRIPTION OF THE DRAWINGS

Since the subject variety is intended to be used only as a rootstock for pear cultivars, the drawings center on the vegetative parts rather than the flowers and fruits.

DESCRIPTION OF VEGETATIVE CHARACTERISTICS

Figure 1:
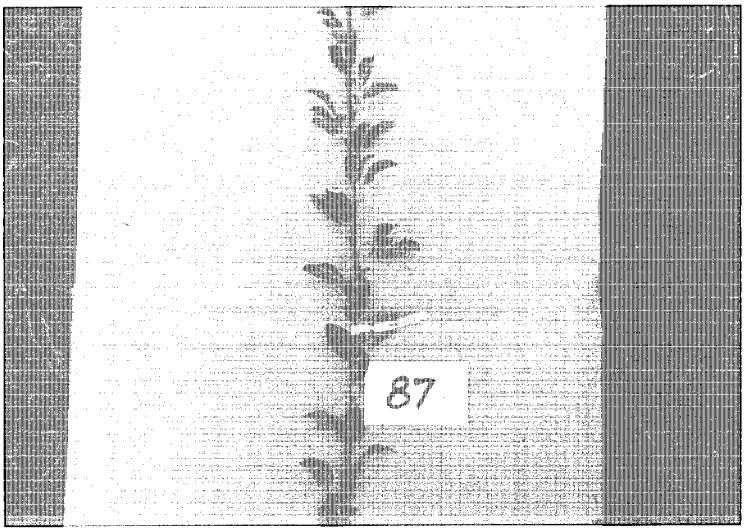
FIG. 1 shows a one-year-old shoot of the subject variety, taken from the cutting bed, showing its straight, upright and branchless habit of growth.
Figure 2:
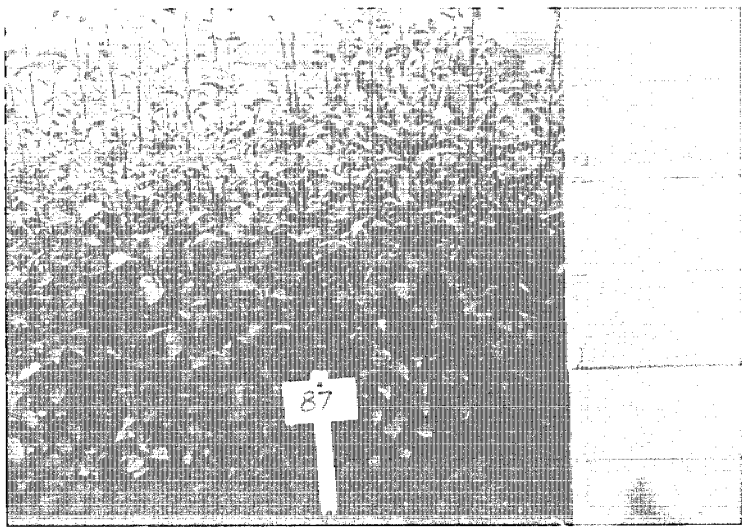
FIG. 2 shows typical leaves and growth of the subject variety in the nursery cutting bed.
Figure 3:
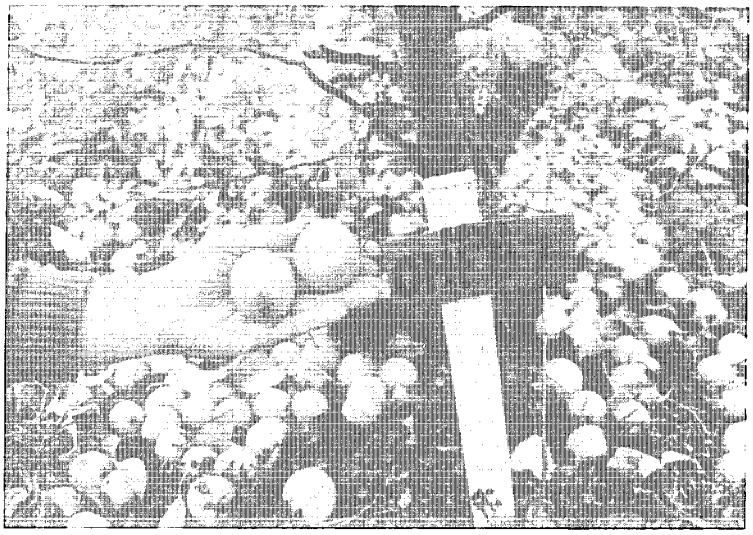
FIG. 3 shows the typical, wide, truncated shaped fruit of the subject variety.
Figure 4:
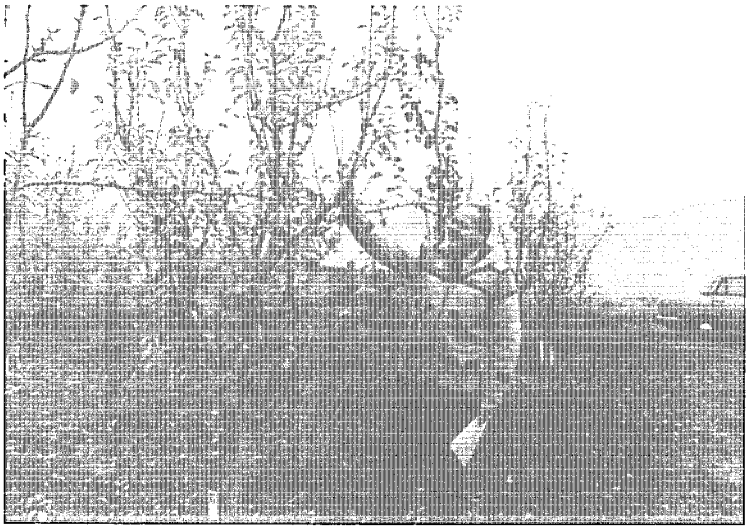
FIG. 4 shows a seven-year-old Bartlett tree on a rootstock of the subject variety.

The following is a detailed description of the new pear rootstock's growth characteristics as observed on one-year-old shoots produced from hardwood cuttings which were grown in a cutting bed located in a propagation nursery at Forest Grove, Oreg. These observations were made during the late growing season after vigorous Summer growth had ceased but prior to Fall leaf senescence. The new variety was also observed closely outdoors in the late Fall during digging operations and again later in a tree storage warehouse where all stocks were evaluated for rooting characters prior to grading and storage. Flower and fruit descriptions were taken from bearing trees growing in experimental test plots at Summerland, British Columbia, Canada. Information listed under "General Characteristics" was taken from numerous test plots scattered throughout several pear growing areas in the United States and in Canada. The characteristics described are those most often seen and used in the identification of a clonally propagated rootstock. Colors of leaves and shoots herein described are based on their appearance at the site where stocks were grown, dug and stored. In those instances where a precise color assessment can be made, reference is to the *Munsell Limit Color Cascade Chart.* In other instances, general color terms are used in accordance with their ordinary dictionary significance.

General habit:
- *Strength of growth.*—Vigorous, willowy, flexible.
- *Habit.*—Upright.
- *Branching.*—Very few, thin, flexible.

Wood — Summer:
- *Color.*—Green (22-11) on upper side, dark green (22-14) on lower side.
- *Pubescence.*—None.
- *Texture.*—Smooth.

Wood — Winter:
- *Stoutness.*—Willowy, flexible.
- *Color.*—Slightly reddish at tips.
- *Diameter of shoots.*—$\frac{1}{4}''$ between buds, 5/16" across buds, 5/16" through buds.
- *Flexibility.*—Flexible.
- *Internodes.*—$1\frac{3}{4}''$, medium.
- *Color.*—Olive-green (23-12) on upper side, brownish-green (23-13) on lower side.
- *Pubescence.*—None.
- *Texture.*—Smooth.

Lenticels:
- *Number.*—Few.
- *Conspicuousness.*—Summer conspicuous.
- *Shape.*—Round, slightly raised.
- *Color.*—Whitish, turning to yellow-brown (27-9).
- *Distribution.*—Scattered.
- *Size.*—Medium.

Leaves:
- *Size.*—Medium, length $2\frac{3}{8}''$, breadth $1\frac{1}{2}''$.
- *Shape.*—Broad elliptic.
- *Base.*—Obtuse, attenuated.
- *Apex.*—Mucronate, sometimes twisted.
- *Serrations.*—Finely serrate.
- *Surface.*—Flat, shiny, few hairs along veins and mid-rib.
- *Margin.*—Slight fold upward.
- *Pose in relation to stem.*—Erect.
- *Color.*—Green (20-14) on upper surface, green (21-11) on lower surface.
- *Pubescence.*—Few hairs along veins and mid-rib on upper surface, none on lower surface.
- *Texture.*—Pliant, smooth upper surface, smooth lower surface.
- *Color of tips of shoots.*—Pale Orange-green (24-8) when still actively growing, becoming reddish in Fall.

Petiole:
- *Pubescence.*—None on upper surface, none on lower surface.
- *Shape.*—Slender, slightly channeled.
- *Length.*—Medium, $\frac{7}{8}''$.
- *Color.*—Green (22-11), pinkish on new growth.
- *Pose.*—Erect.
- *Glands.*—None.

Stipules (not always present):

*Size.*—Small.
*Margin.*—Smooth.
*Length.*—5/16".
*Shape.*—Long, slender.
*Color.*—Light-green (21-10).
*Pose.*—Mostly reposed along petiole.

Buds:
*Size.*—Small.
*Shape.*—Short, obtuse, conical.
*Color.*—Dark-brown, waxy.
*Pubescence.*—None.
*Pose.*—Somewhat appressed.

FLOWER AND FRUIT CHARACTERISTICS

Flowers:
*Size.*—$1\frac{3}{8}$" across in dense clusters, average 8 buds per cluster.
*Color.*—White, occasionally tinged with pink.
*Pedicels.*—$\frac{1}{2}$" long, medium thick, thinly pubescent, green.

Fruit (no commercial value but useful for identification):
*Size.*—$2\frac{1}{8}$" long, $2\frac{1}{8}$" wide.
*Color.*—Yellow (26-4).
*Stems.*—Medium long, medium thick.
*Shape.*—Wide, turbinate, inclined to truncate.

GENERAL CHARACTERISTICS

Rootsuckering: Very rare.

Size control potential: "Semi-dwarf", about 80% of standard, less vigorous varieties more reduced in size.

Yield efficiency: In Northern pear growing areas, averages about 9% above trees on Domestic Seedling stocks (*Pyrus communis* seedlings). Less yield efficient (only slightly above seedling stocks) in Oregon trials.

Compatibility: Graft compatible with all major commercial fruiting varieties.

Rooting: Reproduces well by hardwood cuttings, roots arise at basal cut.

Root anchorage: Excellent in all soil types tested.

Hardiness: Hardy wherever pears are grown.

Disease resistance: Highly resistant to Fireblight (*Erwinia amylovora*), tolerant of the Pear Decline mycoplasma organism, index tested and shown to be free of known pear viruses.

Pest resistance: Average resistance to common pests of pear.

Early bearing ability: Blooms heavily and sets fruit during third growing season.

What is claimed is:

1. A new and distinct variety of pear tree, referred to by the cultivar designation Old Home×Farmingdale No. 87, substantially as herein shown and described, characterized particularly by its ability to serve as a rootstock for grafting of pear tree cultivars to produce "semi-dwarf" pear trees; further characterized by its excellent yield efficiency, its resistance to the Fireblight disease and its tolerance of the Pear Decline disease; further characterized by its hardiness, its excellent root anchorage, its compatibility with all major commercial pear varieties, its early bearing habit, and its ability to root easily and reproduce readily by vegetative means, particularly by hardwood cuttings.

* * * * *